(12) United States Patent
Kermode et al.

(10) Patent No.: US 6,899,685 B2
(45) Date of Patent: May 31, 2005

(54) BIOPSY DEVICE

(75) Inventors: James Kermode, Los Altos, CA (US); Richard L. Mueller, Jr., Jackson, WY (US)

(73) Assignee: Acueity, Inc., Palo Alto, CA (US)

( * ) Notice: Subject to any disclaimer, the term of this patent is extended or adjusted under 35 U.S.C. 154(b) by 127 days.

(21) Appl. No.: 10/351,051

(22) Filed: Jan. 24, 2003

(65) Prior Publication Data

US 2004/0147853 A1 Jul. 29, 2004

(51) Int. Cl.$^7$ ................................................ A61B 10/00
(52) U.S. Cl. ...................... 600/564; 600/570; 600/114; 604/19; 606/167; 606/180
(58) Field of Search ................ 600/562–573, 600/108, 114, 128, 130, 153, 156, 158, 159, 182; 604/19, 27, 35, 43; 606/167, 170, 180

(56) References Cited

U.S. PATENT DOCUMENTS

| | | | | |
|---|---|---|---|---|
| 3,636,940 A | * | 1/1972 | Gravlee | 600/563 |
| 4,243,049 A | * | 1/1981 | Goodale et al. | 600/570 |
| 6,413,228 B1 | * | 7/2002 | Hung et al. | 600/562 |
| 6,500,114 B1 | * | 12/2002 | Petitto et al. | 600/156 |
| 6,689,070 B2 | * | 2/2004 | Hung et al. | 600/562 |
| 2003/0055315 A1 | * | 3/2003 | Gatto et al. | 600/114 |
| 2003/0120176 A1 | * | 6/2003 | Reeves et al. | 600/562 |
| 2003/0181823 A1 | * | 9/2003 | Gatto | 600/564 |

* cited by examiner

*Primary Examiner*—Charles Marmor
(74) *Attorney, Agent, or Firm*—Olson & Hierl, Ltd.

(57) ABSTRACT

A biopsy device suitable for collecting cells from a mammary duct is provided. The device is suitable for conducting brushing biopsy and tissue excision procedures. The device comprises a sheath that is rotatable about a longitudinal axis. The device further comprises an endoscope disposed within and extending through the sheath. An adjustment mechanism is also operatively connected to the endoscope to longitudinally extend and retract the endoscope within the sheath.

15 Claims, 6 Drawing Sheets

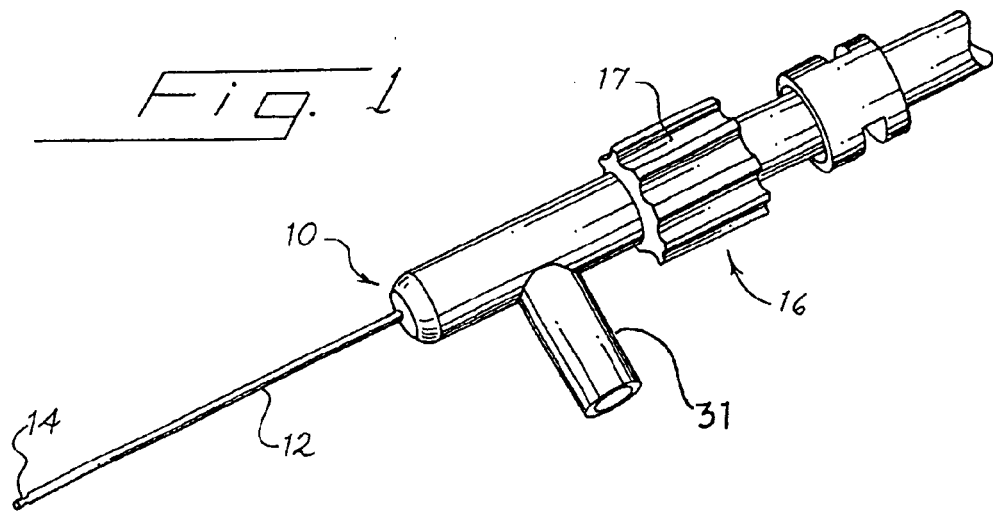
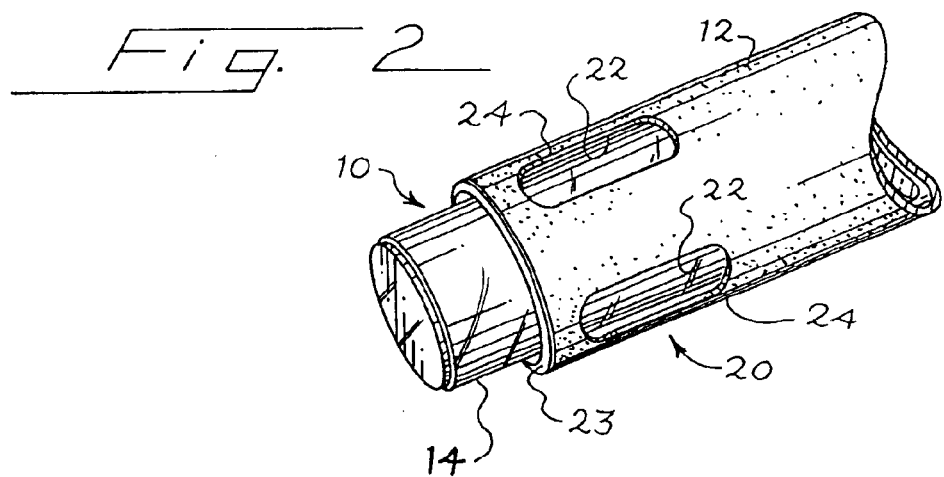
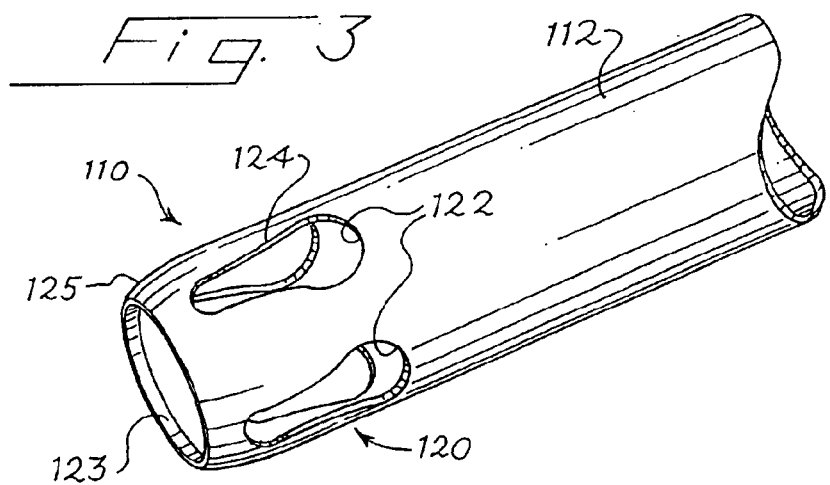

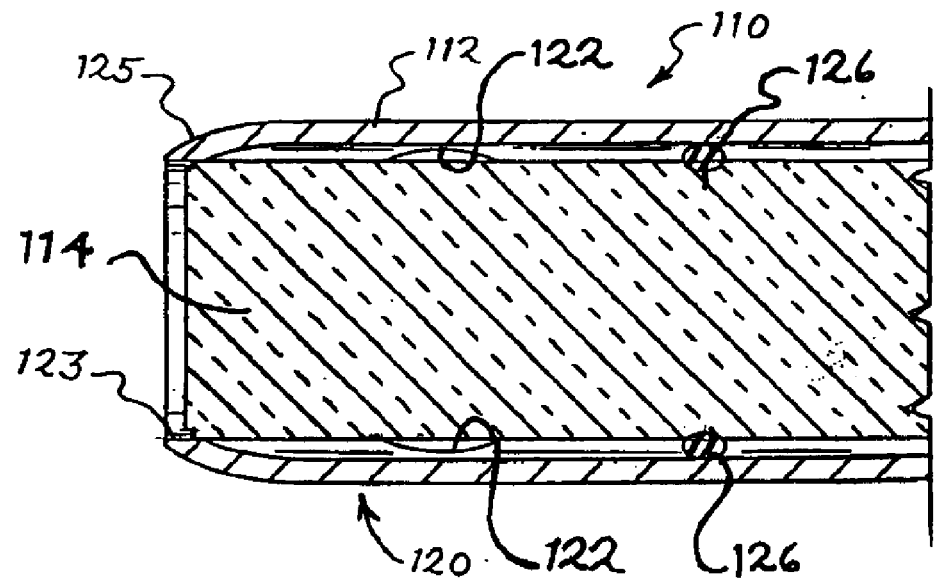
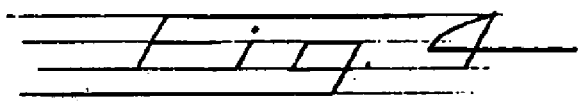
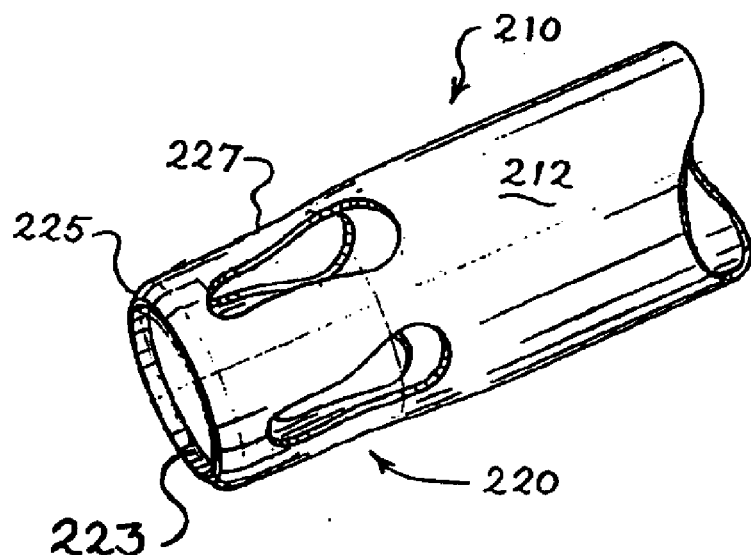
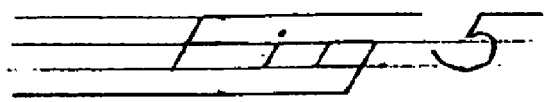

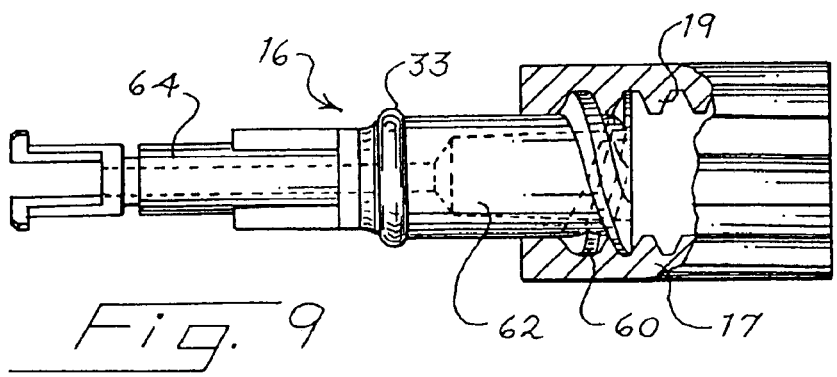
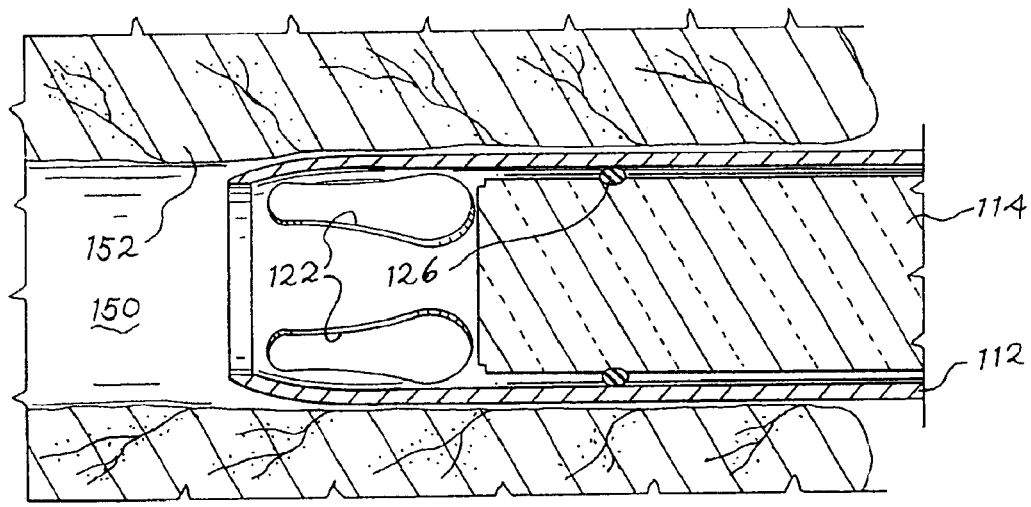
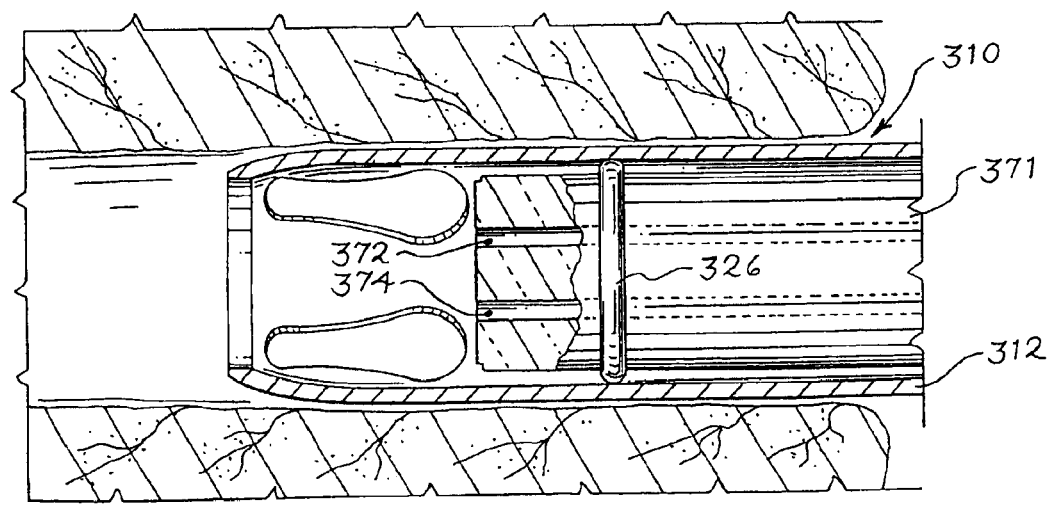

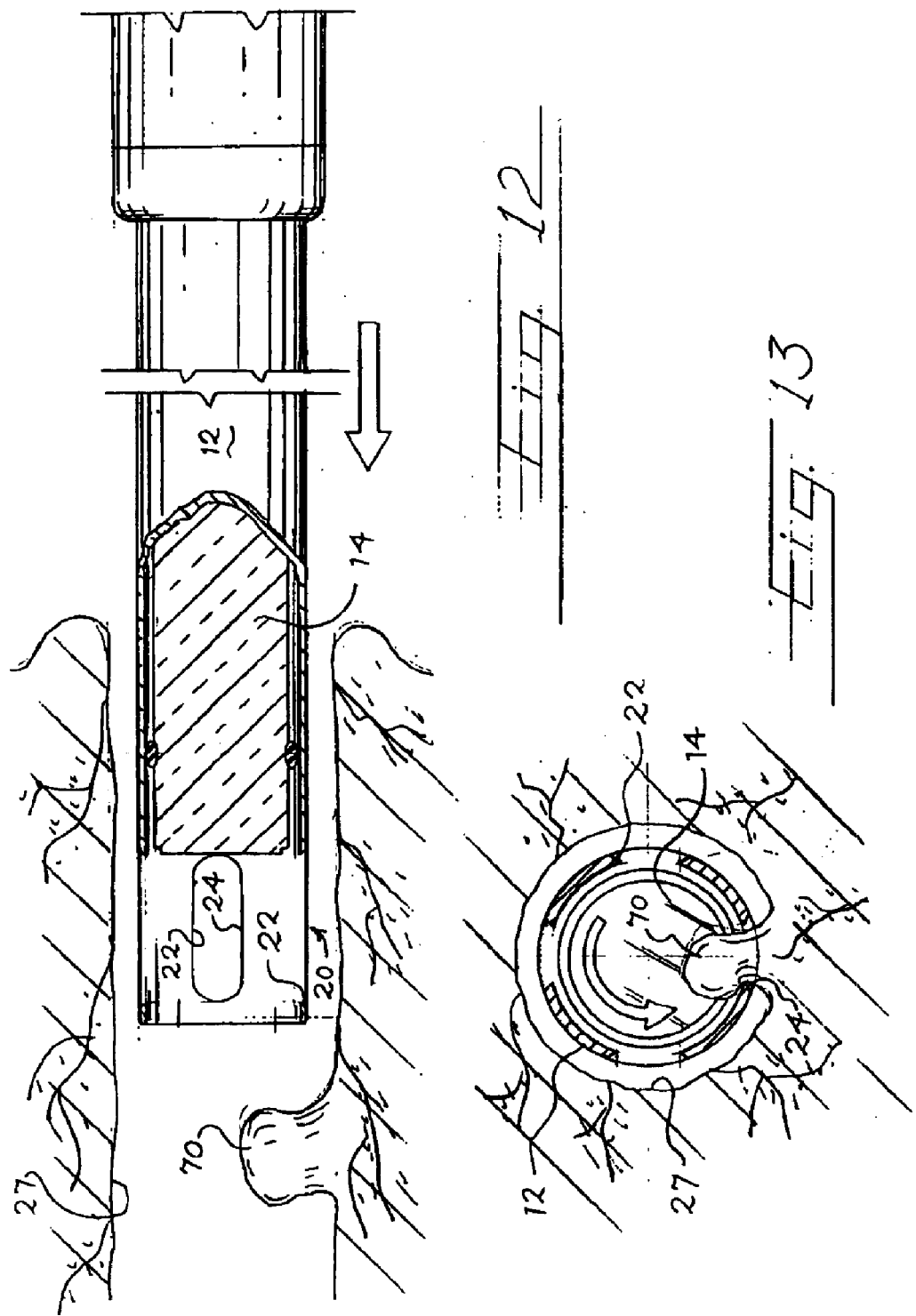

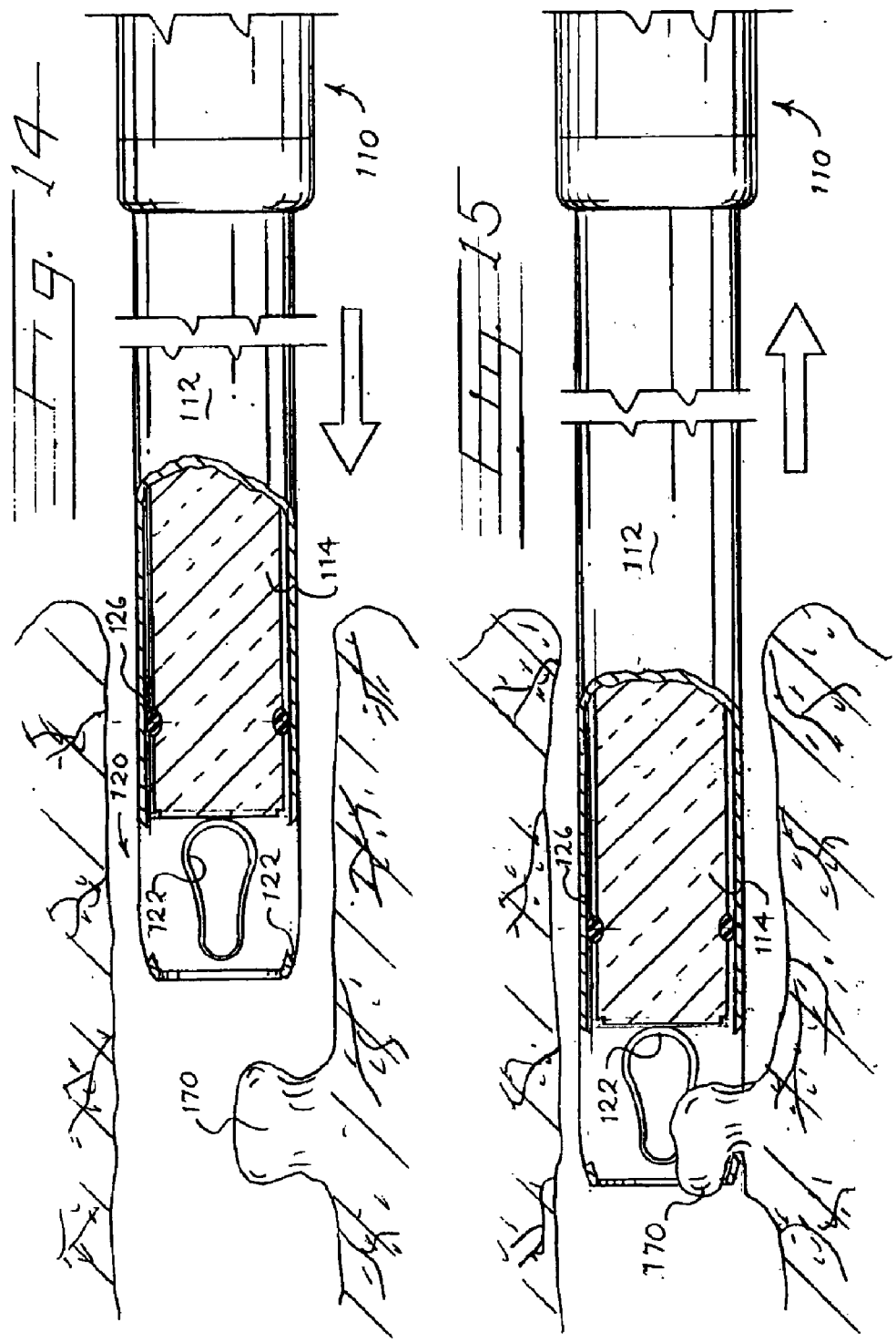

BIOPSY DEVICE

TECHNICAL FIELD OF THE INVENTION

The invention relates to a device for obtaining cytologic samples. More specifically, the invention relates to a biopsy device utilizing a viewing component.

BACKGROUND OF THE INVENTION

Breast cancer is one of the health threats most feared by women, and is the most common form of cancer in women. A key to treatment is early detection. For example, an annual mammogram is a method that has been used in hopes of early detection of breast cancer. One problem with mammography is that such an imaging technique can only find breast cancer once it has taken form. All too often, breast cancer is discovered at a stage that is too far advanced, when therapeutic options and survival rates are severely limited. As such, more sensitive and reliable methods and devices are needed to detect cancerous, pre-cancerous, and other cancer markers of the breast at an early stage. Such methods and devices could significantly improve breast cancer survival. While breast cancer is most common among women, in rare instances the human male may also have occurrences of breast cancer.

Other methods of detecting breast cancer are based on the fact that a vast majority of instances of breast cancer begins in the lining of mammary ducts. Studies have shown that fluid within the mammary duct contains high levels of breast cancer markers, and that an estimated 80%–90% of all breast cancers occur within the intraductal epithelium of the mammary glands. Fluid within the breast ducts contains an assemblage and concentration of hormones, growth factors and other potential markers comparable to those secreted by, or acting upon, the surrounding cells of the alveolar-ductal system. Likewise, mammary fluid typically contains cells and cellular debris, or products that can also be used in cytological or immunological assays. Procedures for obtaining such samples include ductal lavage, expression or aspiration of mammary duct fluid, and collection of mammary duct discharge.

It is sometimes desirable to increase the yield of cells and cellular debris through use of an intraductal brush to loosen and dislodge cellular material from the intraductal epithelium of the mammary glands. An endoscope may be used to guide the brush to the desired region of a mammary duct. The brushing device usually has soft bristles set in twisted strands of wire. Using the wire to pull the bush in opposite directions, the bristles are brushed over the inner wall of the duct at the stricture in an effort to displace cells from the duct wall and capture the cells in the bristles. The soft nature of the bristles and the absence of adequate radial force directing the bristles into the epithelium reduce the likelihood of an adequate yield.

Such brush biopsy devices also offer no papilloma or carcinoma biopsy capability because they cannot effectively excise a tissue sample from the area of stricture. If a particular papilloma or carcinoma is discovered, such as by an endoscopic viewing, a separate procedure needs to be performed to excise and collect a biopsy of the papilloma or carcinoma. For example, a biopsy of the area of the stricture is typically obtained by passing a different instrument, such as biopsy forceps, to the papilloma or carcinoma, and then cutting away and removing the tissue sample. Another method for taking a biopsy of a region in a mammary duct is through the use of a slotted cannula. A distal end of a cannula includes a single opening through which a papilloma or carcinoma may pass. The cannula is rotated or twisted after the papilloma or carcinoma is passed through the window, and thereby the papilloma or carcinoma is excised. A need exists for a device that is capable of performing both a brushing biopsy and an excision without requiring multiple instruments.

SUMMARY OF THE INVENTION

A biopsy device suitable for collecting cells from a mammary duct is provided. The device is suitable for conducting a brushing biopsy, as well as tissue excision procedures. The device comprises an apertured sheath that is rotatable about a longitudinal axis. An endoscope is disposed within the sheath. An adjustment mechanism is operatively connected to the endoscope to longitudinally extend and retract the endoscope within the sheath.

The distal end portion of the sheath defines at least two apertures. The apertures include abrasion edges. The apertures may also be a variety of shapes, but are preferably either pyriform, e.g., pear shaped, or oval and have a major axis, which is aligned to lie along a longitudinal length of the sheath. Additionally, the distal end portion of the sheath may include a roughened surface. The surface may be roughened by any means, such as sandblasting, applying a textured film, or the like. The apertures, and optionally the roughened surface, serve to dislodge cellular material from the epithelium when the sheath is rotated as discussed further below.

The endoscope extends through the sheath and may be extended beyond the distal end of the sheath. Preferably during insertion of the device into a mammary duct, the endoscope is positioned such that the distal end of the endoscope is substantially co-terminus with the distal end of the sheath. As such, the endoscope and sheath will have few, if any, sharp edges on the leading edge of the device and may therefore act as a mammary duct dilator and obturator with minimal risk of injury to the mammary duct. Such precise alignment of the endoscope further permits accurate location of the working end of the device within the mammary duct. The endoscope can also be extended beyond the distal end of the sheath. In order to further lessen the likelihood of ductal injury during the insertion of the device, the distal end portion terminates in an atraumatic tip including a circumferential taper, a circumferential bevel or both.

In a preferred embodiment, the endoscope is extended and retracted within the sheath by an adjustment mechanism controlled by a rotatable positioning hub. It is preferred that the adjustment mechanism is lockable to fix the position of endoscope relative to the sheath.

A brushing biopsy is performed with the present invention by rotating the device within the mammary duct. Prior to insertion of the present invention into the mammary duct, it is preferred that the endoscope is positioned to be substantially co-terminus with the distal end of the sheath. A physician or other medical person views the mammary duct as the device of the present invention is inserted using a viewing device operatively connected to the endoscope, such as a manual lens or a video display. When the distal end portion of the sheath is situated in the desired region of the mammary duct, the physician or other medical person retracts the endoscope to expose the plurality of apertures on the distal end portion of the sheath, and rotates the sheath. In so doing, the edges of the apertures, and in some embodiments a roughened surface of the sheath, act to brush the intraductal epithelium and loosen cytologic material suitable for analysis. Preferably, the endoscope is retracted such that the apertures in the sheath are fully exposed and the physician is able to view the mammary duct to target accurately the desired area or region to be brushed.

The present invention enables a physician also to collect the material dislodged during the brushing biopsy. In one embodiment, a catheter is disposed within the sheath and can be used for removing the dislodged contents of the mammary duct. In this embodiment, the catheter is a double lumen catheter that also introduces a rinsing liquid into the mammary duct, and more preferably, introduces the liquid into the mammary duct while the brushing biopsy is conducted as well as removes the liquid and any cellular materials suspended therein. In another embodiment, introduction of a rinsing liquid and removal of mammary duct contents is achieved by utilizing the sheath itself.

In another embodiment of the present invention, the endoscope includes a circumferential seal, such as an o-ring in a groove, between the endoscope and the interior of the sheath. As the endoscope is fully or partially retracted in the sheath, the distal end portion of the endoscope functions as a piston, such as found within a standard syringe, and draws, i.e., aspirates, a portion of the contents of the mammary duct into the sheath. The device may then be withdrawn with an aliquot of the mammary duct contents retained in the sheath.

Excision of a papilloma or carcinoma can also be performed using the same biopsy device embodying the present invention in a separate procedure, or along with a brushing biopsy procedure. The physician again uses the endoscope to locate the tissue for excision, and then retracts the endoscope. The endoscope is retracted to fully expose the apertures on the distal end portion of the sheath. The papilloma or carcinoma is caused to enter the sheath through one of the apertures. The sheath is then either rotated by the physician or may be pulled or pushed longitudinally within the mammary duct so that the abrasive edges of the apertures excise the papilloma or carcinoma. The excised papilloma or carcinoma can be collected in a manner similar to that discussed above for the brushing biopsy. A papilloma or carcinoma may also be collected by merely withdrawing the device while the excised papilloma or carcinoma is retained within the sheath.

BRIEF DESCRIPTION OF THE DRAWINGS

In the drawings,

FIG. 1 is a perspective view of a biopsy device embodying the present invention;

FIG. 2 is an enlarged, partial view of the distal end portion of the sheath, and an endoscope extending therefrom, of another biopsy device that embodies the present invention;

FIG. 3 is an enlarged, partial view of the distal end portion of the sheath, in a biopsy device embodying the presente invention;

FIG. 4 is an enlarged, partial cross sectional view of the sheath of FIG. 3 and with an endoscope co-terminus with the distal end portion of the sheath;

FIG. 5 is an enlarged, partial perspective view of the distal end portion of the sheath of yet another biopsy device that embodies the present invention;

FIG. 9 is an enlarged, side view of a preferred embodiment of an adjustment mechanism for the biopsy device of the present invention;

FIG. 10 is an enlarged, cross sectional view of the biopsy device embodying the present invention and situated in a mammary duct;

FIG. 11 is an enlarged, cross sectional view of a biopsy device of the present invention equipped with a dual lumen catheter;

FIG. 12 is an enlarged, cross sectional view of the biopsy device shown FIG. 2 before excising a papilloma or carcinoma;

FIG. 13 is an enlarged, cross sectional view of the biopsy device shown FIG. 2 excising a papilloma or carcinoma;

FIG. 14 is an enlarged, cross sectional view of the biopsy device shown FIG. 4 before excising a papilloma or carcinoma; and FIG. 15 is an enlarged, cross sectional view of the biopsy device shown FIG. 4 excising a papilloma or carcinoma.

DESCRIPTION OF THE PREFERRED EMBODIMENT OF THE INVENTION

Figure 6:
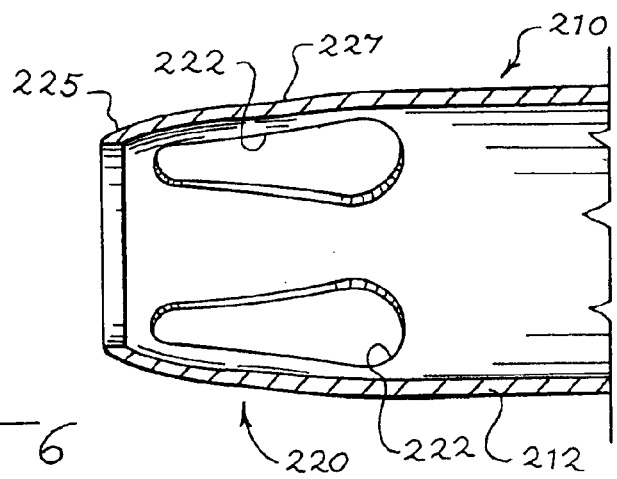
FIG. 6 is an enlarged, partial cross sectional view of the distal end portion of the sheath of a further biopsy device that embodies the present invention.

The invention disclosed herein is susceptible of being embodied in many different forms. Shown in the drawings and described herein below in detail are preferred embodiments of the invention. It is to be understood, however, that the present disclosure is an exemplification of the principles of the invention and does not limit the invention to the illustrated embodiments.

Referring to FIGS. 1 and 2, biopsy device 10 comprises a sheath 12 rotatable about a longitudinal axis and an endoscope 14 extending through the sheath 12. An adjustment mechanism 16 is also operatively connected to the endoscope 14 to longitudinally extend and retract the endoscope 14. The endoscope 14 may act as a dilator as well as an obturator. In a preferred embodiment, the endoscope 14 is extended and retrapted within the sheath 12 by a rotatable positioning hub 17. It is also preferred that the rotatable positioning hub 17 can be locked in place so as to fix the position of endoscope 14 relative to the sheath 12. A flush port 31 is also included through which irrigation liquid can be supplied.

The distal end portion 20 of the sheath 12 defines at least two apertures 22, which include abrasion edges 24. Preferably, the abrasion edges 24 are formed only on transverse edges of the apertures 22. In the embodiment shown in FIG. 2, the apertures 22 are oval, and the major axis of the oval is oriented longitudinally with the longitudinal axis of the sheath 12. As shown in other embodiments below, the apertures such as apertures 22 may be in a variety of shapes. Additionally, the distal end portion 20 of the sheath can include a roughened surface. The surface may be roughened by any means, such as sandblasting, application of a textured film, or the like expedient.

In order to further lessen the likelihood of ductal injury during the insertion or withdrawal of the biopsy device, the distal end 23 can be provided with an atraumatic tip that further includes a circumferential taper, a circumferential bevel, or both.

An embodiment having such an atraumatic tip is shown in FIGS. 3 and 4. The biopsy device 110 includes sheath 112 having a distal end portion 120, again defining apertures 122 having abrasion edges 124. In this particular embodiment the apertures 122 are pyriform or pear-shaped, and the major axis thereof is oriented to lie along the longitudinal axis of the distal end portion 120 of the sheath 112. The apertures 122 are further oriented such that they narrow towards the open distal end 123 of the sheath 112. The distal end 123 of sheath 112 further includes a bevel 125, thereby forming an atraumatic tip. Endoscope 114 is shown co-terminus with sheath 112 in FIG. 4. A circumferential seal 126, such as an o-ring or the like, is optionally situated between sheath 112 and endoscope 114. It is preferred that the o-ring 126 is situated such that when the distal end of endoscope 114 is co-terminus with distal end 123 of sheath 112 or extended beyond the distal end 123, the o-ring 126 is positioned beyond the proximal end of apertures 122 as shown in FIG. 4. As explained in greater detail below, the o-ring can then be used to control the introduction of a rinsing liquid into the mammary duct via the sheath 112 from a flush port such as port 31 shown in FIG. 1. The circumferential seal can co-act with flush port 31 to serve as a two-position valve which allows duct irrigation flow in one position and shutting off irrigation flow in another position. In other words, the circumferential seal is movably positioned within the sheath to control introduction of a liquid into the mammary duct.

Referring to FIGS. 5 and 6, biopsy device 210 has a tapered distal end portion 220 provided with an atraumatic tip which includes both a conical taper 227 and a bevel 225 on the distal end 223 of sheath 212. Apertures 222 are similar to apertures 122 described above.

Figure 7:
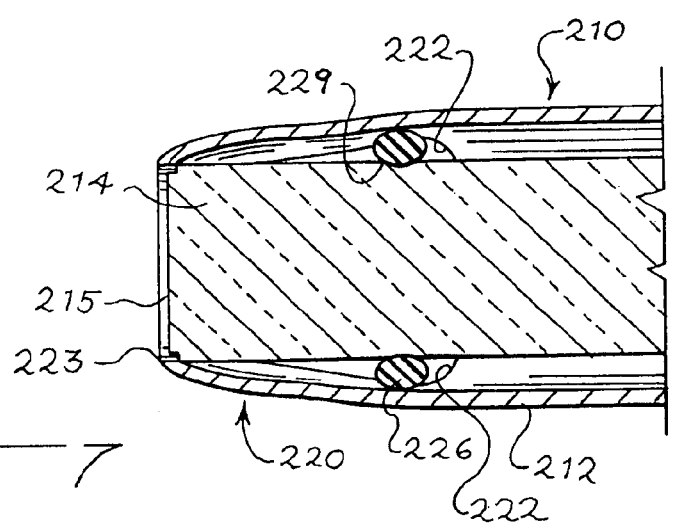
FIG. 7 is an enlarged, partial cross sectional view of the embodiment shown in FIG. 6 with an endoscope co-ternilnus with the distal end portion of the sheath.
Figure 8:
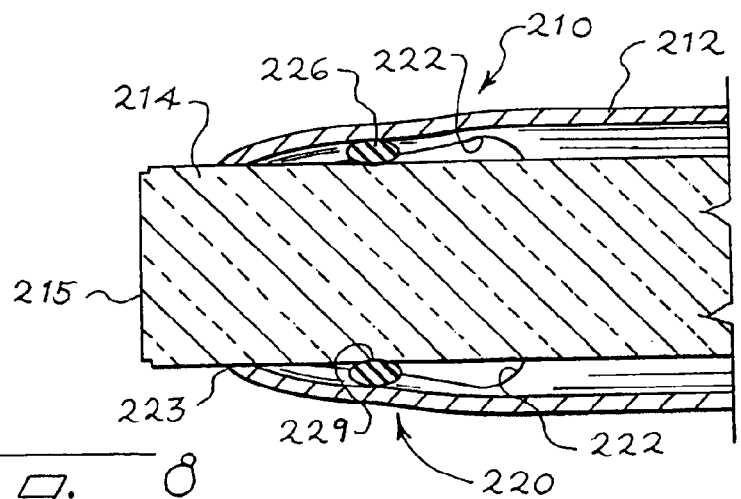
FIG. 8 is an enlarged, partial cross sectional view of the embodiment shown in FIG. 6 with an endoscope extend beyond the distal end portion of the sheath.

As discussed hereinabove, the biopsy device 210 is utilized in a manner that minimizes the potential of damage to the mammary duct during insertion. FIG. 7 shows a preferred method of using the biopsy device. The endoscope 214 is positioned such that it is substantiaUy co-terminus with the distal end portion 220 of the sheath 212. As such, the substantially flat leading edge 215 of the endoscope 214 and the sheath 212 present few, if any, sharp edges to the mammary duct as the biopsy device 210 is inserted therein. After insertion, the endoscope 214 may be extended beyond the distal end 223 of sheath 212 as shown in FIG. 8. Circumferential seal 226 is situated between sheath 212 and endoscope 214 in groove 229 that circumscribes the periphery of endoscope 214.

An adjustment mechanism 16 suitable for extending and retracting an endoscope, such as endoscopes 14, 114 and 214, is shown in FIG. 9. Adjustable mechanism 16 is shown with several cooperating components, including a threaded lead screw 60 threadedly engaged with internal threads 19 in positioning hub 17 and having a mating opening 62 for receiving a viewing device (not shown). An endoscope (not shown) is passed through passage 64 and is secured therein. As the rotatable positioning hub 17 is turned, the threaded lead 60 also rotates to extend or retract an endoscope secured within the passage 64. The adjustment mechanism 16 can also include a rinsing liquid supply and vacuum source control (not shown), such that when the endoscope is moved from an extended first position to a retracted second position, the control is activated.

One of the functions of the present invention is the performance of a brushing biopsy to loosen sections of the intraductal epithelium of the mammary duct for collection and analysis. Referring to FIG. 10, biopsy device 110 comprising a sheath 112 with the same configuration as described with respect to FIGS. 3 and 4 illustrates a brushing biopsy by rotating the sheath 112 within the mammary duct 150. As endoscope 114 is retracted or extended, o-ring 126 moves longitudinally with the endoscope 114. In a preferred embodiment, when endoscope 114 is co-terminus with or extended beyond the distal end 123 of sheath 112, o-ring 126 is positioned beyond the proximal end of aperture 122.

Irrigation liquid may be supplied, such as via port 31 (FIG. 1 ), through the gap between endoscope 114 and sheath 112 and out apertures 122 to clear the viewing field. In still another embodiment, the o-ring or seal can be omitted and a vacuum applied via port 31. A rinsing liquid can also be supplied via port 31. A shut off valve is preferably included in this embodiment to maintain a vacuum as endoscope 14, 114, or 214 is retracted. Also, a rear seal 33 (FIG. 9) can be provided, if desired.

When the distal end portion of the sheath 112 is situated in the targeted region of the mammary duct 150, the endoscope 114 is retracted sufficiently so that the endoscope 114 does not block apertures 122. The physician then rotates the sheath 112. In so doing, the abrasion edges 124 of the apertures 122 act to brush the intraductal epithelium 152 and loosen cytologic material for collection. The procedure can be viewed with the endoscope 114 and particular sections of the intraductal epithelium 152 targeted as desired. Because the process is viewable both before and during brushing, the physician is also able to direct the sheath 112 or manipulate the breast tissue so that the abrasion edges 124 contact the desired region of the intraductal epithelium 152 of the mammary duct 150.

To collect the cytologic material the endoscope 114 includes a circumferential seal, such as an o-ring 126, between the endoscope 114 and the interior of the sheath 112. As the endoscope 114 is retracted in the sheath 112, the contents of the mammary duct are aspirated into the sheath 112. The biopsy device may then be withdrawn along with the aliquot in the sheath 112. As discussed, an alternative embodiment includes a separate vacuum source or a shut off valve to maintain the vacuum as the endoscope 114 is retracted. The movement of the endoscope from a first position wherein the endoscope is co-terminus or extended beyond the distal end of the sheath to a second position wherein the endoscope is co-terminus with a proximal end of the apertures can activate a vacuum source to assist in collecting the brushed material.

Referring to FIG. 11, an alternate embodiment is shown. Biopsy device 310 also comprises a sheath 312 with the same configuration as described with respect to FIGS. 3 and 4. In this embodiment, however, a dual lumen catheter 371 is also disposed within the sheath 312 and is suitable for lavage of a mammary duct. Circumferential seal 326 surrounds catheter 371. In this example, catheter 371 is comprised of lumen 372 and lumen 374. Lumen 372 is suitable for introducing a rinsing liquid, e.g., a saline solution into the mammary duct, whereas lumen 374 is suitable for removing the contents of the mammary duct. It should be understood that a catheter such as catheter 371 can be used with any embodiment of the present invention.

Another feature of the present invention is the capability of excising a papilloma or carcinoma. Referring to FIGS. 12-13, removal of a papilloma or carcinoma utilizing a device of the present invention is illustrated. The biopsy device has substantially the same configuration as that shown in FIG. 2. A section of tissue in mammary duct 27 is identified for excision by the physician. The physician uses the endoscope 14 to locate the target tissue. The endoscope 14 is then retracted to fully expose the apertures 22 in the distal end portion 20 of the sheath 12. The papilloma or carcinoma 70 enters the device through one of the apertures 22 into the sheath 12. Rotation of sheath 12 by the physician causes the abrasion edges 24 to excise the target tissue, such as papilloma or carcinoma 70.

Alternatively, as shown in FIGS. 14–15, a biopsy device 110 such as shown in FIGS. 3–4 having pyriform apertures 122 defined by distal end portion 120 of sheath 112 can be used. Again, the papilloma or carcinoma 170 is received into one of the apertures 122 into the sheath 112. Similar to the previous example, the sheath 112 can be rotated to excise the papilloma or carcinoma 170. The biopsy device 110 may also excise the tissue by retracting the biopsy device from the mammary duct such that the abrasive edges of the aperture 122 excise the papilloma or carcinoma 170.

Collection of an excised papilloma or carcinoma may be accomplished with either of the examples discussed above for the brushing biopsy. A papilloma or carcinoma may also be collected by merely withdrawing the device such that the excised papilloma or carcinoma remains within the sheath.

The foregoing description is to be taken as illustrative, but not limiting. Still other variants within the spirit and scope of the present invention will readily present themselves to those skilled in the art.

We claim:

1. A biopsy device suitable for brushing cells from an epithelium of a mammary duct and for excising tissue from the mammary duct, the biopsy device comprising:
   an apertured sheath rotatable about a longitudinal axis, the sheath having a distal end portion, the distal end portion defining at least two apertures, each aperture including an abrasion edge;
   an extendable and retractable endoscope extending through the sheath; and
   an adjustment mechanism operatively connected to the endoscope to longitudinally extend and retract the endoscope;
   wherein the endoscope further comprises a circumferential seal between the endoscope and the sheath, and wherein the circumferential seal is movably positioned within the sheath to control introduction of a liquid into the mammary duct.

2. The biopsy device of claim 1 further comprising a catheter disposed within the sheath and having a lumen suitable for introducing a liquid into the mammary duct.

3. The biopsy device of claim 1 further comprising a catheter disposed within the sheath and having a lumen suitable for removing a liquid from the mammary duct.

4. The biopsy device of claim 1 further comprising a catheter disposed within the sheath suitable for introducing a liquid into the mammary duct, and for removing contents of the mammary duct.

5. The biopsy device of claim 1, wherein the distal end portion terminates in an atraumatic tip.

6. A biopsy device suitable for brushing cells from an epithelium of a mammary duct and for excising tissue from the mammary duct, the biopsy device comprising:
   an apertured sheath rotatable about a longitudinal axis, the sheath having a distal end portion, the distal end portion defining at least two apertures, each aperture including an abrasion edge;
   an extendable and retractable endoscope extending through the sheath; and
   an adjustment mechanism operatively connected to the endoscope to longitudinally extend and retract the endoscope; wherein the at least two apertures are pyriform, and have a major axis thereof aligned with the longitudinal axis of the sheath.

7. The biopsy device of claim 6 further comprising a catheter disposed within the sheath and having a lumen suitable for introducing a liquid into the mammary duct.

8. The biopsy device of claim 6 further comprising a catheter disposed within the sheath and having a lumen suitable for removing a liquid from the mammary duct.

9. The biopsy device of claim 6 further comprising a catheter disposed within the sheath suitable for introducing a liquid into the mammary duct, and for removing contents of the mammary duct.

10. The biopsy device of claim 6, wherein the distal end portion terminates in an atraumatic tip.

11. A biopsy device suitable for brushing cells from an epithelium of a mammary duct and for excising tissue from the mammary duct, the biopsy device comprising:
    an apertured sheath rotatable about a longitudinal axis, the sheath having a distal end portion, the distal end portion defining at least two apertures, each aperture including an abrasion edge;
    an extendable and retractable endoscope extending through the sheath; and
    an adjustment mechanism operatively connected to the endoscope to longitudinally extend and retract the endoscope; wherein the at least two apertures are oval and have a major axis thereof aligned with the longitudinal axis of the sheath.

12. The biopsy device of claim 11 further comprising a catheter disposed within the sheath and having a lumen suitable for introducing a liquid into the mammary duct.

13. The biopsy device of claim 11 further comprising a catheter disposed within the sheath and having a lumen suitable for removing a liquid from the mammary duct.

14. The biopsy device of claim 11 further comprising a catheter disposed within the sheath suitable for introducing a liquid into the mammary duct, and for removing contents of the mammary duct.

15. The biopsy device of claim 11, wherein the distal end portion terminates in an atraumatic tip.

* * * * *